US007191499B2

(12) United States Patent
Davis et al.

(10) Patent No.: US 7,191,499 B2
(45) Date of Patent: Mar. 20, 2007

(54) MEMORIAL URN

(76) Inventors: David Thomas Davis, 15148 S. Burkstrom Rd., Oregon City, OR (US) 97045; Debbie Ann Davis, 15148 S. Burkstrom Rd., Oregon City, OR (US) 97045; Russell Allen Davis, 441 NW. Ebberts Ave., Hillsboro, OR (US) 97124

( * ) Notice: Subject to any disclaimer, the term of this patent is extended or adjusted under 35 U.S.C. 154(b) by 259 days.

(21) Appl. No.: 10/940,321

(22) Filed: Sep. 14, 2004

(65) Prior Publication Data

US 2005/0246877 A1 Nov. 10, 2005

Related U.S. Application Data

(60) Provisional application No. 60/568,313, filed on May 5, 2004.

(51) Int. Cl.
*A61F 17/00* (2006.01)

(52) U.S. Cl. .............................. 27/1; 40/124.5; 40/722

(58) Field of Classification Search ...................... 27/1; D99/5; 40/725, 718, 722, 746, 124.5
See application file for complete search history.

(56) References Cited

U.S. PATENT DOCUMENTS

| | | | | |
|---|---|---|---|---|
| 4,182,061 | A * | 1/1980 | English | 40/722 |
| 4,199,848 | A | 4/1980 | Kohnert | |
| 4,324,026 | A | 4/1982 | Craft | |
| 5,625,933 | A | 5/1997 | Neuberger et al. | |
| 5,709,441 | A * | 1/1998 | Bartling et al. | 312/107 |
| 5,787,625 | A * | 8/1998 | Yesbick | 40/718 |
| 5,896,632 | A * | 4/1999 | Sturino | 27/1 |
| 5,950,287 | A | 9/1999 | Cacciatore et al. | |
| 5,950,288 | A * | 9/1999 | Bach Lahor | 27/1 |
| D445,557 | S * | 7/2001 | Chang | D99/5 |
| D449,418 | S | 10/2001 | Robinson | |
| 6,347,439 | B1 * | 2/2002 | Bach Lahor | 27/1 |
| 6,526,636 | B2 | 3/2003 | Bernhardt | |
| 6,735,831 | B1 | 5/2004 | Greiwe et al. | |
| D492,079 | S * | 6/2004 | Feltman | D99/5 |
| 6,896,146 | B1 * | 5/2005 | Corrado | 211/85.27 |
| D518,939 | S * | 4/2006 | Borgerding | D99/5 |

* cited by examiner

*Primary Examiner*—William L. Miller
(74) *Attorney, Agent, or Firm*—Chernoff Vilhauer McClung & Stenzel, LLP

(57) ABSTRACT

A combination memorial and storage urn for cremated remains is disclosed, and may include a separate container/support and a pedestal for displaying the memorial.

14 Claims, 5 Drawing Sheets

MEMORIAL URN

The priority of U.S. application Ser. No. 60/568,313 filed May 5, 2004 is claimed.

BACKGROUND OF THE INVENTION

As a tradition dating back thousands of years, memorialization allows survivors to honor their deceased loved ones, preserve a family's heritage, and create a bond between generations. With its origin dating back to the early Stone Age in roughly 3000 B.C., the practice of cremation migrated throughout cultures over the world. Early Christian and Jewish cultures rejected this method of memorialization in favor of earth burial by about 400 A.D. Over the next 1500 years, earth burial dominated the method survivors chose to remember the deceased.

Cremation was revived in the latter half of the 19th century when a dependable chamber to contain cremated remains was created by Professor Brunetti in Italy. After the disclosure of Professor Brunetti's chamber at the 1873 Vienna Exposition, cremation quickly regained popularity in both Europe and North America. With increased concern for health conditions around cemeteries and the ever-increasing costs of earth burials, cremation has become an increasingly popular alternative for the memorialization of the deceased. By 1999, over 25% of all deaths in the United States resulted in cremation of the corpse. As a result of the continually increasing costs, decreasing burial space, and ongoing health concerns, a number of countries and states now mandate cremation as the only option for the memorialization of the deceased.

Cremation presents many options for the family and friends of the deceased. Urns may be placed in a columbarium niche which provides a recessed portion in a wall designed to contain urns. Memorial parks offer designated space for the internment of cremated remains. Most cemeteries also offer patrons the option of space specifically designed for the internment of cremated remains. Many cemeteries will also allow cremated remains to be memorialized in pre-purchased family plots. Other families choose to scatter the ashes of their deceased loved one. Still others opt to remember their loved one by displaying a memorial containing cremated ashes in their homes.

With so many options for creating a unique tribute to the deceased, a strong need exists for tasteful, versatile, and personal memorialization systems to contain cremated remains. This need and others which will become apparent upon consideration of the disclosure herein are met by the present invention.

BRIEF SUMMARY OF THE INVENTION

There are essentially three aspects of the present invention. In a first aspect, a combination memorial and storage urn capable of containing cremated remains consists of a picture frame that provides a display window capable of displaying an image, a recessed or cavity portion within the picture frame, and an ash receptacle secured to a substantially planar back plate. The ash receptacle is received into the recessed portion of the picture frame and the back plate is secured to the picture frame to contain the ash receptacle within the recessed portion of the picture frame. The components of the ash receptacle together form a sealed space capable of containing cremated remains. The back plate may be hung from a generally vertical wall, so as to display the image within the picture frame, or the back plate may be provided with a hinged easel support leg whereby the picture frame/ash receptacle assembly may be displayed on a horizontal surface such as a table or desk.

In a second aspect, the above-described combination memorial and storage urn includes a trapezoidal container capable of containing cremated remains and supporting the combination memorial and urn in a display mode. The trapezoidal container may include an inscription plate capable of being personalized.

In a third aspect, the combination memorial and storage urn includes both the above-described trapezoidal container and a pedestal capable of supporting the combination memorial and urn and trapezoidal container. The pedestal may include an inscription plate capable of being personalized.

Other objects, features, and advantages of the present invention will become apparent from the detailed description which follows taken in conjunction with the accompanying drawings.

DETAILED DESCRIPTION OF PREFERRED EMBODIMENTS

Figure 1:
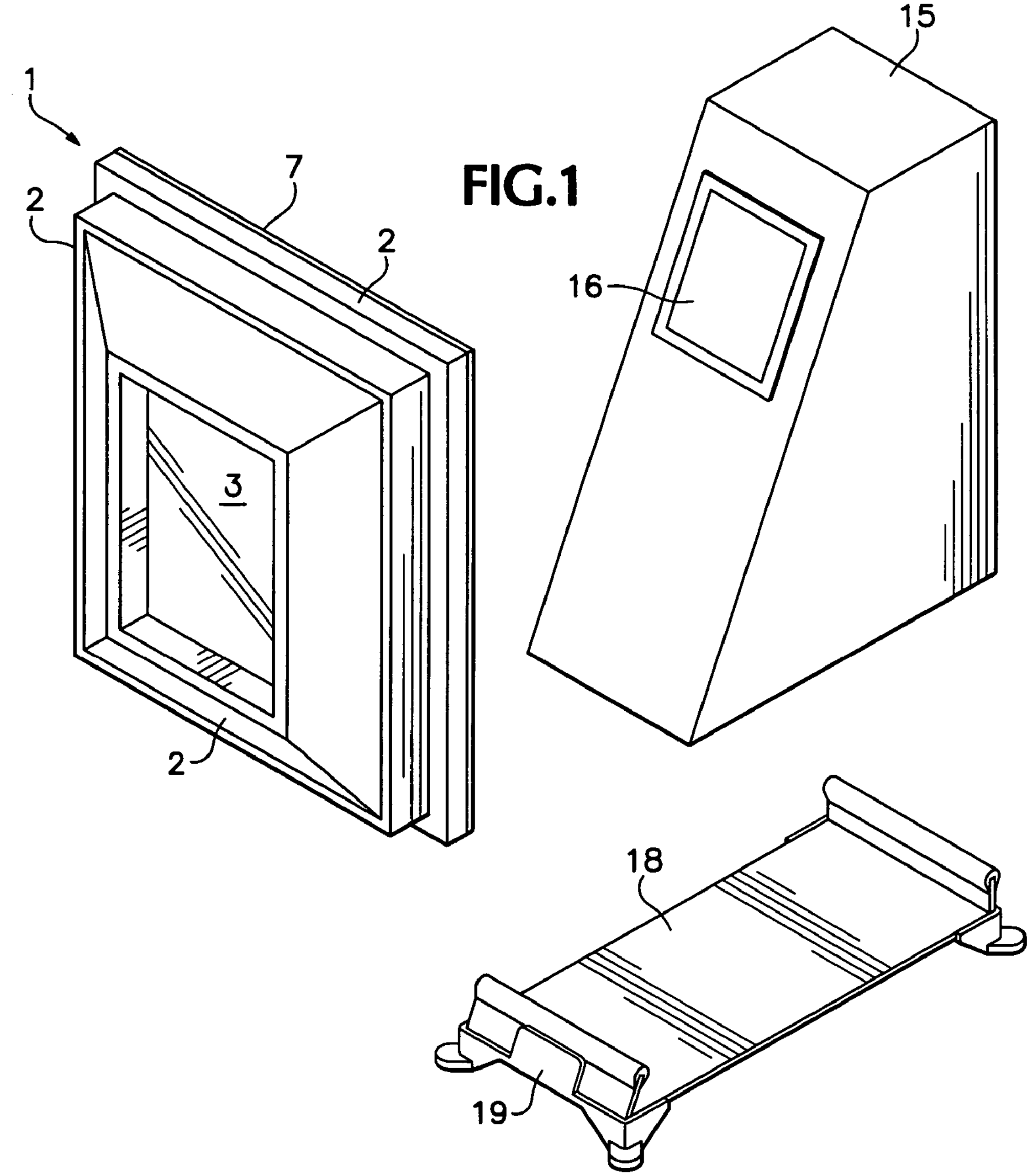
FIG. 1 is a perspective view of the three basic components making up the memorial system of the invention.

Referring now to the drawings, wherein the same numerals refer to like elements, there is shown in FIGS. 1–6 a combination memorial and storage urn 1 consisting of a picture frame 2 having a cavity on its back side for receiving an ash receptacle 10 and a back plate 7 for securing the ash receptacle to the picture frame, a trapezoidal container 15, and a support pedestal 18. Trapezoidal container 15 is capable of supporting the picture frame and attached ash receptacle 10 in a display-like manner. Pedestal 18 is capable of supporting both the trapezoidal container and the picture frame and its attached ash receptacle in a display-like manner.

Figure 2:
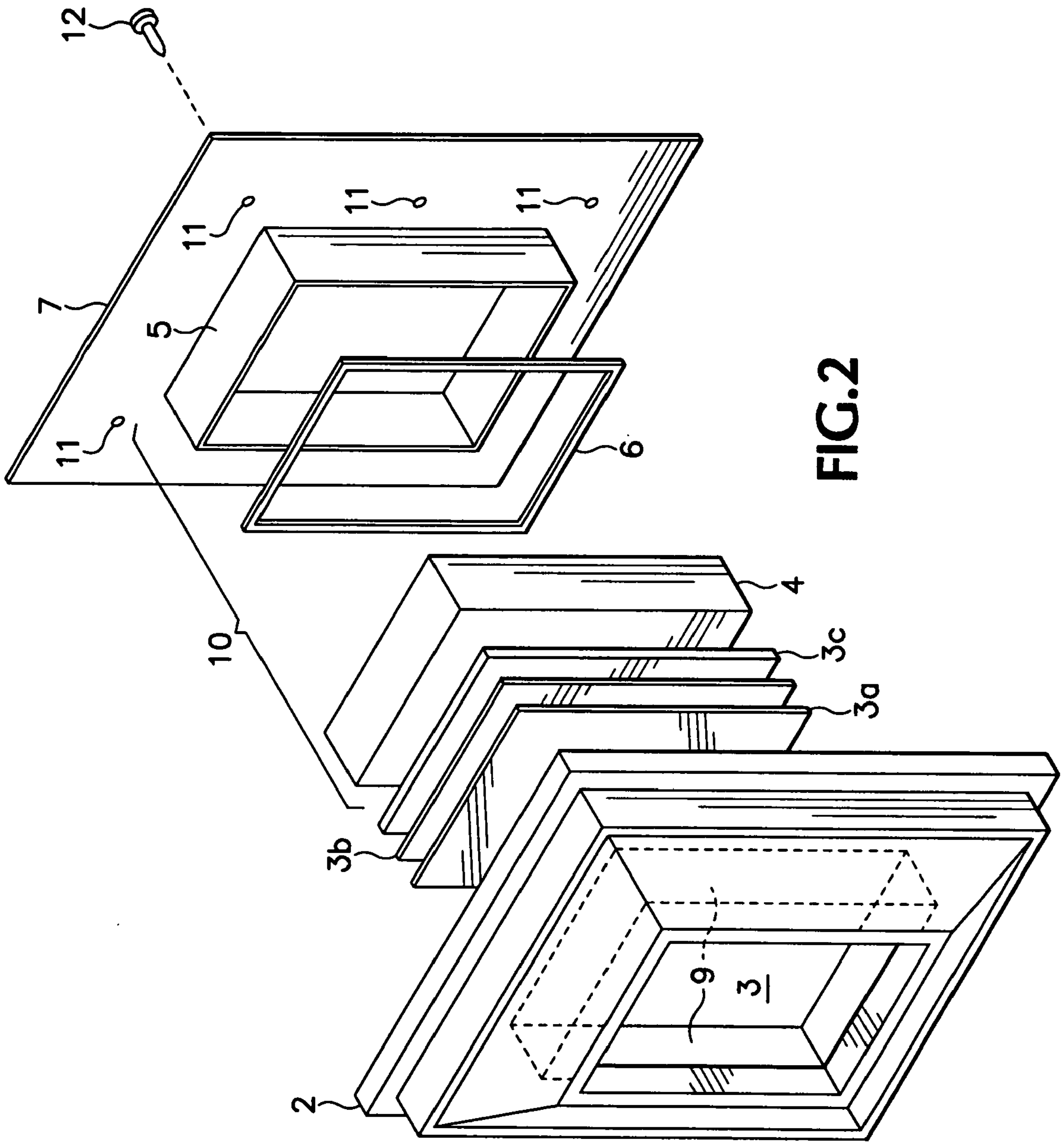
FIG. 2 is a perspective assembly view showing unassembled components of the picture frame/ash receptacle assembly of the invention.
Figure 3:
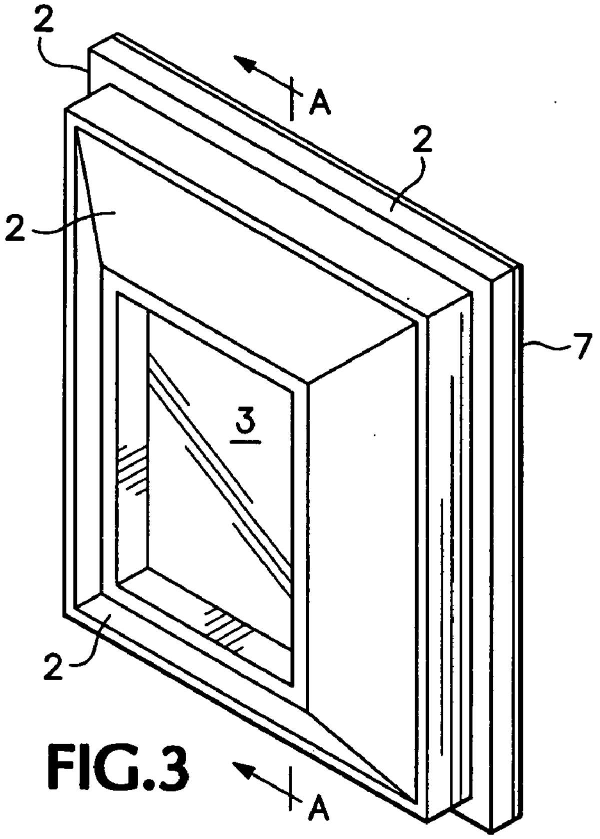
FIG. 3 is a perspective view of the assembled picture frame/ash receptacle assembly of FIG. 2.
Figure 4:
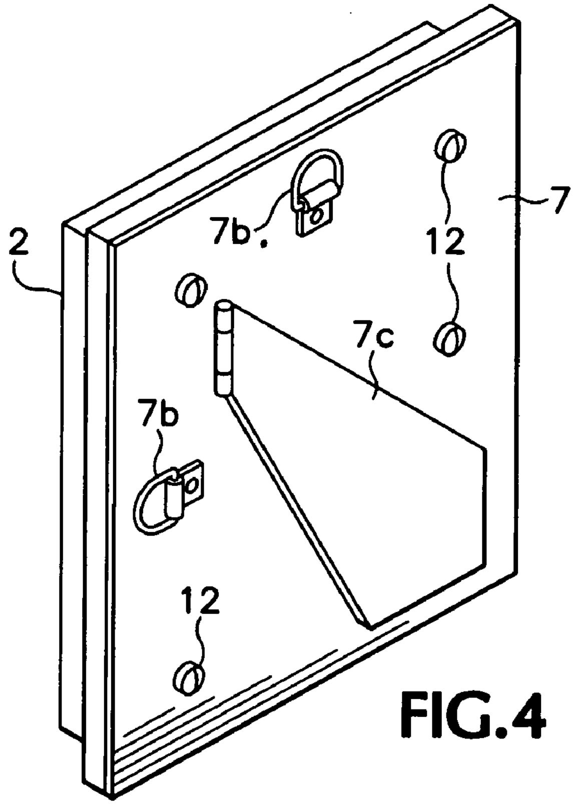
FIG. 4 is a perspective view of the back side of the assembly shown in FIG. 3.
Figure 5:
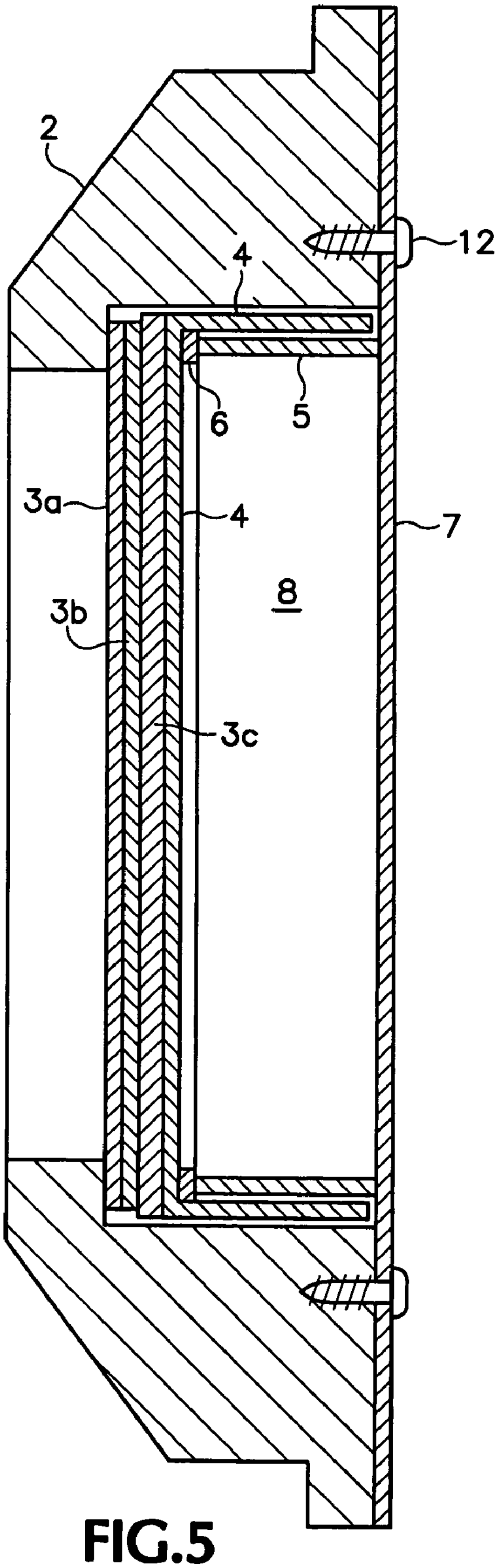
FIG. 5 is a sectional view of FIG. 3 taken through the plane 5-5.

FIG. 2 shows details of the picture frame and its attached ash receptacle. The picture frame includes a display window 3, with its associated elements transparent protective covering 3*a*, photo or portrait 3*b*, optional matting (not shown) and optional resilient spacer 3*c*. Ash receptacle 10 consists of components 4 and 5, gasket 6 and back plate 7. Gasket 6 is preferably secured within the confines of component 4 so as to be engaged by the periphery of the walls of component 5 as shown in FIG. 5, but could also be secured to the inner periphery of component 5, shown as second gasket 6*a* in FIG. 6.

Figure 6:
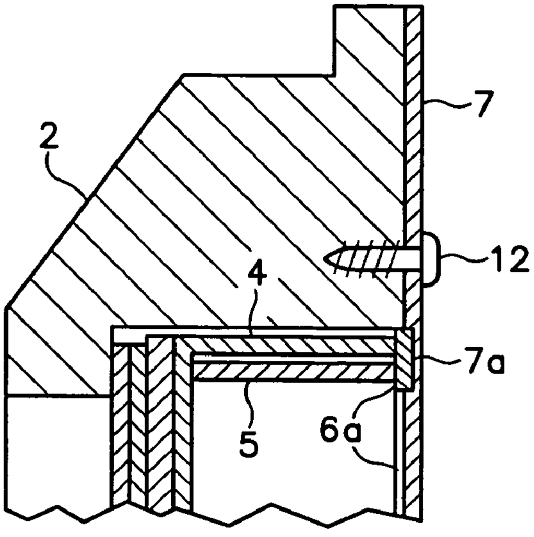
FIG. 6 is another sectional view of FIG. 3 showing an alternative embodiment of the ash receptacle component of the invention.

Back plate 7 may be secured to component 5 by soldering, welding or by adhesive. Alternatively, back plate 7 may have a recessed gasket seat 7*a* therein that corresponds to the footprint of components 4 and 5; in such an alternative embodiment, second gasket 6*a* has a slightly thicker periphery, allowing it to snugly seat in gasket seat 7*a* and to be situated between back plate 7 and components 4 and 5, as shown in FIG. 6.

The back side of the picture frame is provided with a recessed cavity 9 for receiving the ash receptacle. When components 4 and 5 and back plate 7 of the ash receptacle are fitted together under compression, they form a sealed space 8 that is capable of containing cremated remains.

Picture frame 2 may be made from any suitable material such as wood, metal, plastic, or ceramic. Display window 3 is capable of displaying an image that is protected by a sheet of transparent material 3*a* between the inside of the picture frame and the image. Picture frame 2, cavity 9, ash receptacle 10 and back plate 7 are all preferably generally rectilinear, but it should be understood that they may be in virtually any shape, including polyhedral, round or oval. If desired, picture frame 2 may include decorative fluting, stippling or painting.

Ash receptacle 10 preferably fits flush with the back side of picture frame 2 by virtue of the back plate 7 being secured to the picture frame so as to form a substantially planar back surface. Back plate 7 may be secured to the back side of picture frame 2 by pre-drilled and threaded screw holes 11 with screws 12. Back plate 7 may be provided with one or more hangers 7*b* so as to allow the picture frame/ash receptacle assembly to be hung from a wall. The assembly may also be displayed on a generally horizontal surface such as a table or shelf either by providing the back plate with a hinged easel support leg 7*c* or by supporting it with trapezoidal container 15.

Figure 7:
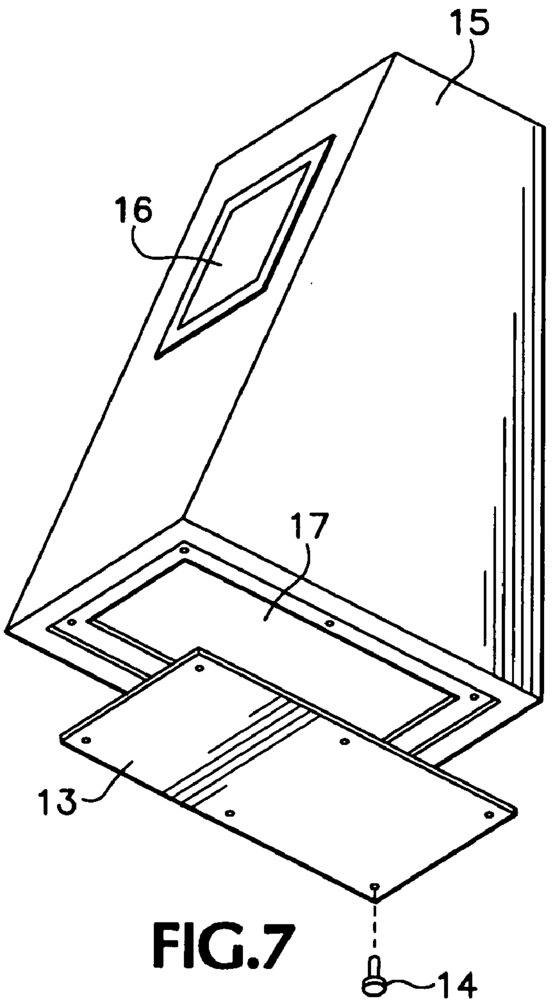
FIG. 7 is an underside perspective view of the trapezoidal container component of the invention with detachable bottom plate.

Referring to FIG. 7, trapezoidal container 15 is made from a suitable material capable of containing cremated remains, such as wood, metal or polymer. Trapezoidal container 15 is preferably provided with an opening 17 on one of its surfaces through which cremated remains may be placed for containment and storage. Opening 17 is preferably covered over with a plate 13 and gasket (not shown) secured to an indentation in the container's wall with suitable fastening means such as by screws 14, so as to fit flush with the container's wall. An inscription plate 16 may be secured to the trapezoidal container 15 for personalization. When filled with cremated remains, trapezoidal container 15 is sufficiently heavy to support the picture frame/ash receptacle assembly by simply leaning the assembly against the angled front side of the trapezoidal container. The trapezoidal container containing cremated remains may also be buried in the ground by itself.

Figure 8:
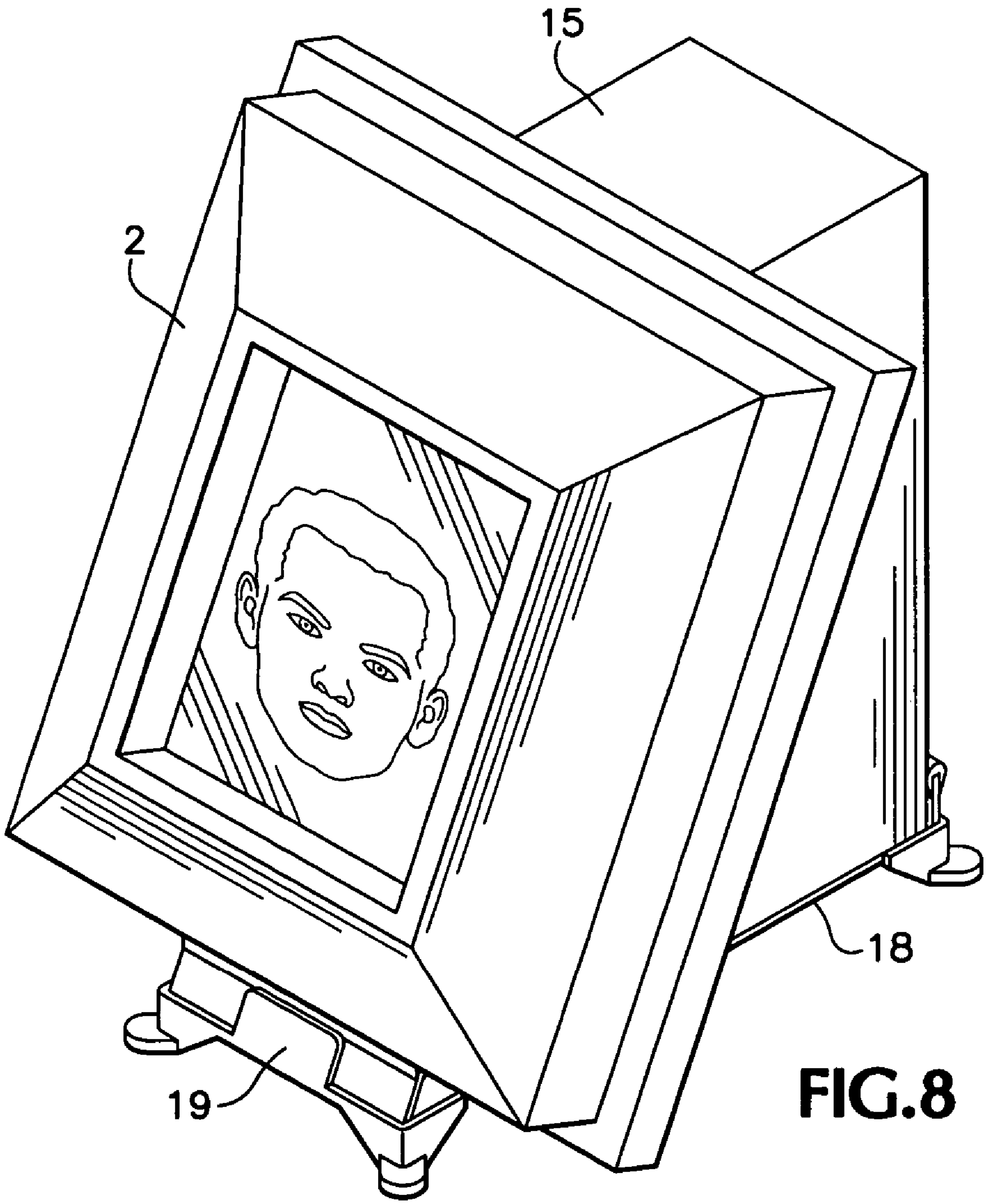
FIG. 8 is a perspective view of the three components shown in FIG. 1 assembled in a display mode.

Finally, a pedestal 18 (shown in FIGS. 1 and 8) may also be included to support trapezoidal container 10 and the picture frame/ash receptacle assembly for display purposes. An inscription plate 19 may be secured to pedestal 18 for personalization.

Collectively, the picture frame/ash receptacle assembly, the trapezoidal container, and the pedestal constitute a system of components that compliment each other to create a meaningful memorial to the deceased.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A combination memorial and storage urn for cremated remains comprising the following components:
(a) a frame member providing a display window capable of displaying an image;
(b) a sealable ash receptacle for containing cremated remains secured to a substantially planar back plate;
(c) a cavity in said frame member capable of receiving said sealable ash receptacle wherein said sealable ash receptacle comprises two open-ended receptacles nestable one within the other and separated by a gasket in sealing engagement with both of said two open-ended receptacles.

2. The urn of claim 1 wherein said back plate is attachable to and detachable from said frame member.

3. The urn of claim 2 wherein said back plate engages with said frame member to create a sealed space.

4. The urn of claim 1 wherein said back plate is provided with at least one hanger so as to allow the urn to be hung from a generally vertical wall.

5. The urn of claim 1 wherein said back plate is provided with an easel support leg so as to allow the urn to be supported on a generally horizontal surface.

6. The urn of claim 1 wherein said frame member, said ash receptacle, said cavity and said back plate are in a shape selected from rectilinear, polygonal, oval and round.

7. The urn of claim 6 wherein said shape is selected from a rectangle and a square.

8. The urn of claim 1 wherein said image is in the form of a photograph.

9. The urn of claim 1 wherein said image is in the form of a portrait.

10. A combination memorial and storage system for cremated remains comprising the following components:
(a) a frame member providing a display window capable of displaying an image;
(b) a sealable ash receptacle for containing cremated remains secured to a substantially planar back plate;
(c) a cavity in said frame member capable of receiving said sealable ash receptacle; and
(d) a trapezoidal container capable of containing cremated remains and supporting said frame member and said sealable ash receptacle.

11. The system of claim 10 wherein said trapezoidal container displays a memorial inscription plate.

12. A combination memorial and storage system for cremated remains comprising the following components:
(a) a frame member providing a display window capable of displaying an image;
(b) a sealable ash receptacle for containing cremated remains secured to a substantially planar back plate;
(c) a cavity in said frame member capable of receiving said sealable ash recptacle;
(d) a trapezoidal container capable of containing cremated remains and supporting said frame member and said sealable ash receptacle; and
(e) a pedestal capable of supporting said frame member and said sealable ash receptacle and said trapezoidal container.

13. The system of claim 12 wherein said trapezoidal container displays a memorial inscription plate.

14. The system of claim 13 wherein said pedestal displays a memorial inscription plate.

* * * * *